(12) United States Patent
Jang et al.

(45) Date of Patent: *May 16, 2006
(10) Patent No.: US 7,044,964 B2

(54) CATHETER SYSTEM HAVING IMAGING, BALLOON ANGIOPLASTY, AND STENT DEPLOYMENT CAPABILITIES, AND METHOD OF USE FOR GUIDED STENT DEPLOYMENT

(75) Inventors: Yue-Teh Jang, Fremont, CA (US); Stephen M. Salmon, Sunnyvale, CA (US); David A. White, San Jose, CA (US); Rizza A. Garcia, San Jose, CA (US)

(73) Assignee: Cardiovascular Imaging Systems, Inc., Sunnyvale, CA (US)

( * ) Notice: Subject to any disclaimer, the term of this patent is extended or adjusted under 35 U.S.C. 154(b) by 576 days.

This patent is subject to a terminal disclaimer.

(21) Appl. No.: 10/306,976

(22) Filed: Nov. 27, 2002

(65) Prior Publication Data
US 2003/0105509 A1 Jun. 5, 2003

Related U.S. Application Data

(60) Continuation of application No. 09/384,846, filed on Aug. 27, 1999, now abandoned, which is a division of application No. 08/880,947, filed on Jun. 23, 1997, now Pat. No. 6,074,362, which is a division of application No. 08/556,660, filed on Nov. 13, 1995, now Pat. No. 5,749,848.

(51) Int. Cl.
*A61F 2/06* (2006.01)

(52) U.S. Cl. ........................ 623/1.2; 623/902

(58) Field of Classification Search ........ 604/507–510, 604/96.01, 500, 264, 523; 606/192, 194, 606/198, 28; 600/207, 470, 466, 467, 463; 623/1.11, 1.12, 902, 903, 1.2
See application file for complete search history.

(56) References Cited

U.S. PATENT DOCUMENTS 4,733,665 A 3/1988 Palmaz .................. 128/343

(Continued)

OTHER PUBLICATIONS

*European Heart Journal* (1998) 19, 1122-1124, " Is there MUSIC in IVUS guided stenting? Is this MUSIC going to be a MUST?".

(Continued)

*Primary Examiner*—Cris Rodriguez
(74) *Attorney, Agent, or Firm*—Orrick Herrington & Sutcliffe LLP (57) ABSTRACT

A catheter system has a balloon angioplasty device disposed about a common lumen near its distal end. The balloon catheter is pre-fitted with a stent which is deployed when the balloon is inflated. The common lumen is in communication with multiple lumens within a proximal region of the catheter body to allow for positioning of the catheter over a movable guide wire and convenient delivery of imaging or interventional devices to a desired region of a body passageway being treated. The procedure for stent deployment optionally includes steps of imaging a lumen by ultrasound before and after stent deployment to identify the site at which a stent is needed, to confirm that the stent is being and has been deployed at a longitudinal position which does not overlap a branched segment of the body passageway, and to ensure that the stent has been radially opened to an optimum diameter.

11 Claims, 7 Drawing Sheets

U.S. PATENT DOCUMENTS

| | | | |
|---|---|---|---|
| 4,794,931 A | 1/1989 | Yock | |
| 4,795,458 A | 1/1989 | Regan | |
| 4,800,882 A | 1/1989 | Gianturco | |
| 4,856,516 A | 8/1989 | Hillstead | |
| 4,886,062 A | 12/1989 | Wiktor | |
| 4,951,677 A | 8/1990 | Crowley et al. | 128/662.05 |
| 5,000,185 A | 3/1991 | Yock | |
| 5,095,911 A | 3/1992 | Pomeranz | 128/662.06 |
| 5,115,814 A | 5/1992 | Griffith et al. | 128/662.06 |
| 5,158,548 A | 10/1992 | Lau et al. | 604/96 |
| 5,190,046 A | 3/1993 | Shturman | |
| 5,192,307 A | 3/1993 | Wall | |
| 5,207,695 A | 5/1993 | Trout, III | |
| 5,219,335 A | 6/1993 | Willard et al. | 604/164 |
| 5,224,953 A | 7/1993 | Morgentaler | 606/192 |
| 5,243,988 A | 9/1993 | Sieben et al. | 128/662.06 |
| 5,257,974 A | 11/1993 | Cox | 604/96 |
| 5,292,321 A | 3/1994 | Lee | |
| 5,313,949 A | 5/1994 | Yock | |
| 5,314,408 A | 5/1994 | Salmon et al. | 604/22 |
| 5,325,860 A | 7/1994 | Seward et al. | 128/662.06 |
| 5,327,885 A | 7/1994 | Griffith | |
| 5,344,426 A | 9/1994 | Lau et al. | |
| 5,345,940 A | 9/1994 | Seward et al. | 128/662.06 |
| 5,350,395 A | 9/1994 | Yock | 606/194 |
| 5,353,798 A | 10/1994 | Sieben | 128/662.06 |
| 5,364,347 A | 11/1994 | Jang | |
| 5,368,035 A | 11/1994 | Hamm et al. | |
| 5,405,377 A | 4/1995 | Cragg | |
| 5,411,016 A | 5/1995 | Kume et al. | |
| 5,456,694 A | 10/1995 | Marin et al. | |
| 5,458,615 A | 10/1995 | Klemm et al. | |
| 5,582,178 A | 12/1996 | Yock | 128/662.06 |
| 5,651,364 A | 7/1997 | Yock | 128/660.03 |
| 5,660,180 A | 8/1997 | Malinowski et al. | 128/660.03 |
| 5,676,151 A | 10/1997 | Yock | |
| 5,682,897 A | 11/1997 | Pomeranz | 128/662.06 |
| 5,749,848 A | 5/1998 | Jang et al. | |
| 5,817,102 A | 10/1998 | Johnson et al. | 606/108 |
| 5,836,965 A | 11/1998 | Jendersee et al. | 606/198 |
| 5,865,178 A | 2/1999 | Yock | |
| 5,902,245 A | 5/1999 | Yock | |
| 5,980,530 A | 11/1999 | Willard et al. | 606/108 |
| 5,980,533 A | 11/1999 | Holman | 606/108 |
| 5,997,523 A | 12/1999 | Jang | 604/462 |
| 6,050,949 A | 4/2000 | White et al. | 600/466 |
| 6,068,634 A | 5/2000 | Lorentzen Cornelius et al. | 606/108 |
| 6,077,273 A | 6/2000 | Euteneuer et al. | 606/108 |
| 6,117,104 A | 9/2000 | Fitz | 604/96.01 |
| 6,126,685 A | 10/2000 | Lenker et al. | 623/1 |
| 6,165,127 A | 12/2000 | Crowley | 600/463 |
| 6,168,617 B1 | 1/2001 | Blaeser et al. | 623/1.11 |
| 6,217,586 B1 | 4/2001 | Mackenzie | 606/108 |
| 6,234,971 B1 | 5/2001 | Jang | 600/462 |
| 6,261,246 B1 | 7/2001 | Pantages et al. | 600/585 |
| 6,296,622 B1 | 10/2001 | Kurz et al. | 604/93.01 |
| 6,306,096 B1 | 10/2001 | Seward et al. | 600/463 |
| 6,364,840 B1 | 4/2002 | Crowley | 600/463 |
| 6,364,841 B1 | 4/2002 | White et al. | 600/466 |
| 6,371,962 B1 | 4/2002 | Ellis et al. | 606/108 |
| 6,375,676 B1 | 4/2002 | Cox | 623/1.16 |
| 6,394,978 B1 | 5/2002 | Boyle et al. | 604/103.06 |
| 6,419,685 B1 | 7/2002 | Di Caprio et al. | 606/192 |
| 6,432,130 B1 | 8/2002 | Hanson | 623/1.11 |
| 6,451,052 B1 | 9/2002 | Burmeister et al. | 623/1.16 |

OTHER PUBLICATIONS

*European Heart Journal* (1998) 19, 1124-1125, "Improving outcomes in heart failure".

*European Heart Journal* (1998) 19, 1214-1223, "Intravascular ultrasound-guided optimized stent deployment".

EndoSonics brochure entitled "MegaSonics OTW PTCA Catheter".

FIG. 14

CATHETER SYSTEM HAVING IMAGING, BALLOON ANGIOPLASTY, AND STENT DEPLOYMENT CAPABILITIES, AND METHOD OF USE FOR GUIDED STENT DEPLOYMENT

This application is a continuation application of U.S. Ser. No. 09/384,846 filed on Aug. 27, 1999, now abandoned which is a divisional of U.S. Ser. No. 08/880,947 filed on Jun. 23, 1997 which issued as U.S. Pat. No. 6,074,362, which is a divisional of U.S. Ser. No. 08/556,660 filed on Nov. 13, 1995 which issued as U.S. Pat. No. 5,749,848 on May 12, 1998.

FIELD OF THE INVENTION

The present invention relates generally to guided stent deployment using a catheter system for imaging and treatment of stenoses within a body passageway, including a patient's vascular system, and more particularly to a catheter system in which an angioplasty balloon can be used to deploy a stent device, said catheter system further including an imaging element for use within a region of a blood vessel so that placement and expansion of the stent can be observed.

DESCRIPTION OF THE BACKGROUND ART

Arteriosclerosis, also known as atherosclerosis, is a common human ailment arising from the deposition of fat-like substances, referred to as atheroma or plaque, on the walls of blood vessels. Such deposits occur both in peripheral blood vessels that feed limbs of the body and coronary blood vessels that feed the heart. Localized accumulation of deposits within regions of the blood vessels may result in stenosis, or narrowing of the vascular channel. When this occurs, blood flow is restricted and the person's health is at serious risk.

Numerous approaches for treating such vascular deposits have been proposed, including balloon angioplasty, in which a balloon-tipped catheter is used to dilate a stenosed region within the blood vessel; atherectomy, in which a blade or other cutting element is used to sever and remove the stenotic material; laser angioplasty, in which laser energy is used to ablate at least a portion of the stenotic material; and the like.

Where removal of vascular deposits is not desired, endovascular grafts have been developed to enlarge an occluded vessel lumen, and to hold tissue in place or to provide a support for a graft while healing is taking place. Intraluminal endovascular grafting has been shown to provide an alternative to conventional vascular surgery. Endovascular grafting involves percutaneous insertion of a prosthetic graft into a blood vessel, and such devices are generally delivered via a catheter to a region of interest within the vascular system. These techniques have the clear advantage over conventional surgery of eliminating a need for surgically exposing, replacing, incising, removing, or bypassing a defective blood vessel. Several structures have been shown to have use as intraluminal prosthetic grafts. These structures include coiled stainless steel springs, helically wound coil springs, and expanding stainless steel stents.

In order to apply certain intervention techniques more effectively, a variety of vascular imaging devices and methods may be employed. Of particular interest to the present invention, imaging catheters having ultrasonic transducers at their distal ends have been employed to produce images of the stenotic region from within the blood vessel.

A number of specific designs for ultrasonic imaging catheters have been described. An early design is illustrated in U.S. Pat. No. 4,794,931, where the mechanical components of the imaging system are located within a housing at the distal end of the catheter. The housing includes a fixed guidewire at its distal tip, which is used to position the catheter within the vascular system. While the use of such fixed-guidewire designs can provide excellent image quality, under some circumstances it is desirable to use an "over-the-wire" design where the catheter may be introduced over a separate (movable) guidewire. The use of a movable guidewire offers certain advantages, including improved steering capability through narrow regions and easier catheter exchange, e.g., substitution of an interventional catheter for the imaging catheter.

Various designs for removable and non-removable imaging cores have also been described. Specific examples are set forth in Sieben et al., U.S. Pat. No. 5,243,988, and in Sieben et al., U.S. Pat. No. 5,353,798, both of which are incorporated herein by reference. These devices generally include an imaging core designed to operate within a guidewire lumen of therapeutic catheters which accept a guidewire of 0.018 inch or smaller. In one embodiment, the device consists of a fixed, non-removable proximal hub apparatus, which is not disconnectable from the imaging core. The main body of the device consists of the drive shaft, and this shaft provides for ease of loading the imaging core into the therapeutic catheter, and steady rotational movement in order to obtain an image without distortion.

Exchanging the imaging catheter for an interventional or other catheter within a patient's vascular system is time consuming and may be injurious to the patient. It is desirable therefore to combine imaging and interventional capabilities in a single catheter system. A design for an ultrasonic imaging catheter having a balloon angioplasty device is described in U.S. Pat. No. 5,117,831. One depicted embodiment uses a fixed guidewire and is thus subject to the disadvantages noted above. Another embodiment has a guidewire movable through the ultrasonic imaging transducer and is associated drive shaft. This requires that the transducer and is associated drive shaft and not movable along the length of the catheter.

To be able to cross very narrow lesions, the diameter of the catheter should be as small as possible at its distal end. Furthermore, the need to move the catheter body within the patient should be minimized. The blood vessel interior is delicate, may be weakened by disease, and is therefore susceptible to injury from movement of the catheter body within it.

Despite the availability of devices for imaging a body passageway as described above, there is a dearth of techniques for guided placement of prosthetic devices, including stents, within a body passageway, including the vascular system. The vasculature of the human body is highly curved and includes many branches in vessels. It is moreover undesirable to place a prosthetic device in a branched segment of a blood vessel for at least two reasons. First, a prosthetic device such as a stent will, in time, accumulate endothelial cell growth which will clog the wire mesh of the stent. If the stent is located at a vessel branch point, then the stent, once clogged, will act as an impermeable barrier to blood flow into the vessel which branches away from the main vessel. Second, if a later episode of vascular disease occurs in the vessel which branches away from the main vessel, then the stent which is located at the vessel branch point will block access to the branched vessel, and will thereby preclude the later use of a vascular catheter as an interventional therapy for this branched blood vessel.

The present techniques for guided placement of a prosthetic device within a vessel rely on X-ray imaging or fluoroscopy to visualize the location of the stent, and angiography using a radiopaque substance to visualize the branch points of blood vessels. This technique suffers from the serious disadvantage that the prosthetic device or stent is detectable by fluoroscopy only when the device is constructed from metal which is sufficiently thick. However, the thickness of metal needed for fluoroscopic detection causes the prosthetic device to be too stiff to safely navigate the tortuous passageways of blood vessels. For this reason, the presently available techniques for guided placement of stents cannot be utilized with the most widely used and most preferred stents; flexible stents adapted for entry into narrow and highly curved blood vessels, such as the Palmaz-Schatz stent available from Johnson & Johnson. For these reasons, approximately 95% of the stents which are in wide use today are not radiopaque.

For the reasons stated above, it would be advantageous to provide a catheter system having a balloon angioplasty system with a prosthetic device such as a vascular graft or stent associated therewith, in combination with visualization capabilities for guided placement of the prosthetic device within a region of interest within the vascular system. Such delivery should be accomplished with a minimum repositioning of the catheter body within the blood vessel. Additionally, the catheter should be as narrow as possible at its distal end to allow for entry into and through narrow and tortuous regions of the patient's vascular system.

SUMMARY OF THE INVENTION

The present invention provides a catheter system having the ability to deliver both an angioplasty balloon and another work element for imaging or treating a region within a patient's vascular system, said catheter system further having the ability to implant a stent in the vascular system and to perform a guided stent placement procedure. The catheter system comprises a catheter body having a proximal and a distal region. The proximal region has at least two lumens, one for carrying a movable guidewire and another for carrying a work element. The work element will typically be an ultrasonic imaging transducer but may be another imaging device or even an interventional device for treating the blood vessel in combination with the angioplasty balloon. The distal region of the catheter body has a common lumen connected to and in communication with the two lumens of the proximal region. The angioplasty balloon is disposed about the common lumen of the distal region, and the catheter system further includes a prosthetic device, such as a vascular graft or a stent, associated with said balloon, and an associated means for inflating the balloon, typically an inflation lumen extending from the proximal end of the catheter body to the balloon. The prosthesis will generally be flexible, and have a tubular shape with proximal and distal ends, and may include a metallic wire mesh. The prosthesis will typically be crimped onto the balloon so that it is disposed closely about the balloon, and is capable of controlled radial expansion in a region of interest upon the application of a radial, outwardly extending force from the interior of the prosthesis.

In an alternative embodiment, the catheter has one or more lumens in the proximal region, and the movable guidewire is secured to the distal region of the catheter with a monorail type catheter design as disclosed by Yock, U.S. Pat. No. 5,350,395, incorporated herein by reference. In this design, the movable guidewire is not carried by any of the one or more lumens in the proximal region.

Another alternative catheter has one or more lumens in the proximal region, and two or more lumens in the distal region of the catheter, wherein at least one of the proximal lumens is in communication with at least one of the distal lumens. In this embodiment, the guidewire occupies one lumen in the distal region and can remain in place during imaging. This design offers the convenience of imaging using a movable imaging core in the second distal lumen while the guidewire remains in place in the first distal lumen. Operations using this design save time associated with withdrawing and advancing of instruments through the various lumens, but suffer the small drawback of displaying an image having artifacts associated with the presence of the guidewire positioned at one location in the ultrasound scan.

The catheter of the present invention will allow for performance of rapid and convenient balloon angioplasty and imaging for guided placement of a prosthetic device or stent within a diseased vessel, while minimizing the need to reposition the catheter body between procedures. Additionally, the distal end of the catheter will be relatively narrow to allow for movement of the catheter into restricted spaces of the patient's vascular system and particularly into narrow regions and stenoses within the coronary arteries. Further, the catheter of the invention enables stent deployment in combination with balloon angioplasty and imaging, and will allow for a guided stent placement procedure.

An alternative catheter is equipped with a self-expanding prosthetic device, such as a stent, which is composed of a shape retaining metal, such as nitinol. This catheter may generally include a means for retaining the self-expanding prosthesis so that it is disposed radially closely about the balloon. Retaining means may be provided in the form of a sheath disposed about the distal region of the catheter body so that the prosthesis is operatively associated with the sheath. In one embodiment, the prosthesis may be disposed between the catheter body and the sheath so that when the sheath is removed, the prosthesis is released and automatically enlarges to an expanded diameter. When a self-expanding prosthesis is employed, an angioplasty balloon is not required on the catheter for enlarging the prosthesis, but may be included where balloon angioplasty is desired in combination with stent deployment. The self-expanding prosthesis is installed on the catheter at a first diameter which permits intraluminal delivery of the prosthesis into a body passageway and which places the prosthesis in close proximity to the catheter body. The prosthesis has a shape memory which allows it to expand to a larger diameter when the means for retaining the prosthesis are removed.

The present invention also provides methods for guided positioning and deployment of prosthetic devices, including intraluminal grafts and stents, to a region of interest within a body passageway without use of fluoroscopy or angiography. The methods employ a catheter having proximal and distal ends with an angioplasty balloon or a sheath disposed about the distal region. The catheter further includes a prosthesis such as an intravascular graft or a stent associate with the balloon or the sheath. The stent may be constructed from metal, and may be crimped onto the balloon or disposed between the sheath and the catheter body so that it is disposed closely about the distal region of the catheter body. According to one method, the catheter may be advanced into a body passageway until the prosthesis lies within a region of interest. An ultrasound transducer is then used to image the proximal edge of the prosthesis, the distal edge of the prosthesis, or both edges of the prosthesis to ensure that the prosthesis is positioned at a desired location, and particularly to verify that the prosthesis does not overlap with a branching segment of the body passageway. If the observed position of the prosthesis is suboptimal, the longitudinal position of the catheter may be adjusted to relocate the balloon and the associated prosthesis so it is clear of the branching segment of the body passageway. Repositioning of the prosthesis may also be desirable to achieve proper overlap of the prosthesis on each side with healthy segments of a blood vessel. The prosthesis is then deployed, either by inflating the balloon to controllably expand the prosthesis at the region of interest, or by removing the sheath, whereby the self-expanding prosthesis enlarges. The catheter is then removed from the body passageway, thereby leaving the implanted prosthesis or stent in place. Where an angioplasty balloon is used, the balloon must be deflated before removing the catheter from the region of interest.

An alternative method for guided deployment of a prosthetic device in a body passageway using the catheters of the invention may include the step of advancing a guidewire into the blood vessel until a distal end of the guidewire lies within a stenosed region or a region having a lesion, and a proximal end of the guidewire extends from the patient. The proximal end of the guidewire may then be loaded into the common lumen of the distal region of the catheter body, into a guidewire lumen, or into the monorail lumen, and then the catheter is advanced over the guidewire into the blood vessel until the prosthesis associated with the distal region of the catheter lies within the region of interest. Where a common lumen catheter is employed, the guidewire may be retracted out of the common lumen and into the proximal region of the catheter body. An ultrasonic imaging transducer and associated drive shaft may then be advanced through a lumen of the proximal region of the catheter body and into the common lumen. Where a monorail catheter or a catheter having at least two lumens at the distal region is employed, then the guidewire need not be withdrawn to allow access by the ultrasonic imaging transducer, but the guidewire may be withdrawn to improve image quality. The ultrasonic imaging transducer may be provided in the form of a removable imaging core or a non-removable imaging core. The transducer is then activated to provide images of at least one of the proximal and distal ends of the prosthetic device to ensure that the prosthesis is positioned at a desired location, away from a branching segment of the blood vessel, and overlapping with healthy segments of the vessel, on both sides of the prosthesis. The catheter is then removed from the body passageway, thereby leaving the implanted prosthesis or stent in place. Where an angioplasty balloon is used, the balloon must be deflated before removing the catheter from the region of interest.

The invention also provides methods for implanting a prosthesis within a body passageway using the catheters of the invention so that optimal radial expansion of the prosthesis may be achieved. The catheter is positioned within a body passageway so that the prosthesis associated with the distal region of the catheter lies within a region of interest. The balloon is inflated to controllably expand the prosthesis at the region of interest. An ultrasound transducer is provided in the region of the angioplasty balloon, and said transducer is activated to obtain images of the prosthesis while disposed about the inflated balloon, and thereby provide a first diameter of the expanded prosthesis. The balloon may then be deflated, whereby the prosthesis is permitted to recoil. The internal region of the prosthesis is then imaged again to determine a second diameter to ensure the expanded prothesis has maintained a sufficiently large opening after recoil. In this manner, if the recoil diameter is smaller than the desired diameter, the balloon can be reinflated to a second diameter larger than the first diameter, such that after recoil, the desired diameter is achieved. For example, if a 10% recoil in diameter occurs, the balloon can be reinflated to a diameter which is greater than the desired diameter by an amount so that, after a 10% recoil occurs, a final diameter of precisely that desired is achieved.

In an alternative embodiment where a self-expanding prosthesis is employed, the catheter is positioned within a body passageway so that the prosthesis which is associated with the distal region of the catheter lies within the region of interest. The prosthesis is released at the region of interest by withdrawing the sheath, or by any other known means to release a self-expanding prosthesis, whereby the prosthesis expands. The expanded prosthesis is then imaged to determine a first diameter of the expanded prosthesis. If this diameter is not sufficiently large, then a second prosthesis can be inserted within the first prosthesis to further enlarge the diameter of the first prosthesis.

DETAILED DESCRIPTION

The prosthetic devices which are preferred for use with the catheters and methods described herein include stents, and particularly the Palmaz-Schatz stent which is available from Johnson & Johnson. Stents for use herein are disclosed in Palmaz, U.S. Pat. No. 4,733,665, and Cragg, U.S. Pat. No. 5,405,377, both of which are expressly incorporated herein by reference. Briefly, these stents include a tubular-shaped member having first and second ends and a wall surface disposed between the first and second ends, the wall surface being formed by a plurality of intersecting elongate members, at least some of the elongate members intersecting with one another intermediate the first and second ends of the tubular-shaped member; the tubular-shaped member having a first diameter which permits intraluminal delivery of the tubular-shaped member into a body passageway having a lumen; and the tubular-shaped member having a second, expanded diameter, upon the application from the interior of the tubular-shaped member of a radially, outwardly extending force, which second diameter is variable and dependent upon the amount of force applied to the tubular-shaped member, whereby the tubular-shaped member may be expanded to expand the lumen of the body passageway. Methods for deploying prosthetic devices, including stents, are disclosed in Lau et al., U.S. Pat. No. 5,158,548, and in Cox, U.S. Pat. No. 5,257,974, both of which are expressly incorporated herein by reference.

The prosthetic devices may be composed of a shape retaining or shape memory material such as nitinol so that the devices are self-expanding and thermally activatable within a vessel upon release from a retaining means which holds the prosthetic device in a compressed state at the first diameter. These devices will automatically expand to a second, expanded diameter upon being released. The construction and deployment of a self-expanding stent is disclosed in Morgentaler, U.S. Pat. No. 5,224,953, which is expressly incorporated herein by reference.

The plurality of elongate members may be a plurality of wires, and the wires may be fixedly secured to one another where the wires intersect with one another. The plurality of elongate members may be a plurality of thin bars which are fixedly secured to one another where the bars intersect with one another. The tubular-shaped member may have a biologically inert coating on its wall surface, and the coating may include a means for anchoring the tubular-shaped member to the body passageway.

The catheters for use herein include those described in Jang, U.S. Pat. No. 5,364,347, and Willard et al., U.S. Pat. No. 5,219,335, both of which are expressly incorporated herein by reference. The catheters may comprise an elongate catheter body having proximal and distal ends and at least two regions, a proximal region and a distal region. The proximal region of the catheter body may have at least two lumens extending at least partly therethrough. The distal region of the catheter body will have a single common lumen in communication with both of the lumens of the proximal region. Additionally, an inflatable angioplasty balloon will be disposed about the common lumen of the distal region of the catheter, and a prosthetic device, vascular graft, or stent will be releasably disposed about the angioplasty balloon, or associated therewith.

In use, a catheter will be advanced over a guidewire into a patient's vascular system. First the guidewire will be advanced alone into the patient until the guidewire lies within a particular region of interest. This will typically be a region in which a blood vessel has been narrowed by a stenotic lesion. The distal end of the guidewire will be advanced into the region of stenosis with the proximal end of the guidewire remaining outside of the patient's body. The proximal end of the guidewire may then be inserted into the distal end of the catheter body and fed through the common lumen of the distal region. When the proximal end of the guidewire reaches a transition region between the distal and proximal region of the catheter body, the guidewire will be directed into a particular guidewire lumen of the proximal region.

Once the guidewire has been directed into the guidewire lumen, the catheter will be advanced into the patient's vascular system until the prosthetic device associated with the distal region lies within the region of interest. During advancement of the catheter into the blood vessel, the proximal end of the guidewire will exit the catheter body through a guidewire port located some distance proximal of the distal region (in either an "over-the-wire" configuration, or a "monorail" configuration). The proximal end of the guidewire may then be grasped and pulled back sufficiently to withdraw the distal end of the guidewire into the guidewire lumen and clear of the common lumen of the distal region. An ultrasonic imaging transducer or other work element may then be advanced through another lumen of the proximal region and into the common lumen for imaging the region of interest.

Prior to inflation of the balloon, the imaging transducer is activated to determine the position of the proximal edge of the prosthesis, the distal edge of the prosthesis, or both edges of the prosthesis. This step is performed for the purpose of determining whether the prosthetic device overlaps with a branching segment of the blood vessel so that the balloon and its associated prosthetic device can be repositioned away from the branching segment before inflation of the balloon and deployment of the prosthetic device. The exact positioning of the prosthetic device is also important because it is desirable to have the prosthetic device extend longitudinally at both its proximal and distal ends to healthy segments of the blood vessel. It is difficult to determine exactly where the diseased segment of the blood vessel begins and ends without ultrasound imaging from within the body passageway.

Thus, a catheter according to the present invention will allow for the convenient delivery of a balloon angioplasty device and an associated prosthetic device in combination with another interventional or imaging device to a region of interest within the patient. Because the catheter uses a single common distal lumen, it may be made with a reduced profile at its distal end. This will allow delivery of the balloon angioplasty, associated stent, imaging, or other interventional devices even within narrow, tortuous regions of the patient's vascular system. Furthermore, the various work elements are delivered through a common lumen lying within the balloon, thus minimizing the need to reposition the catheter body between treatment steps.

Figure 1:
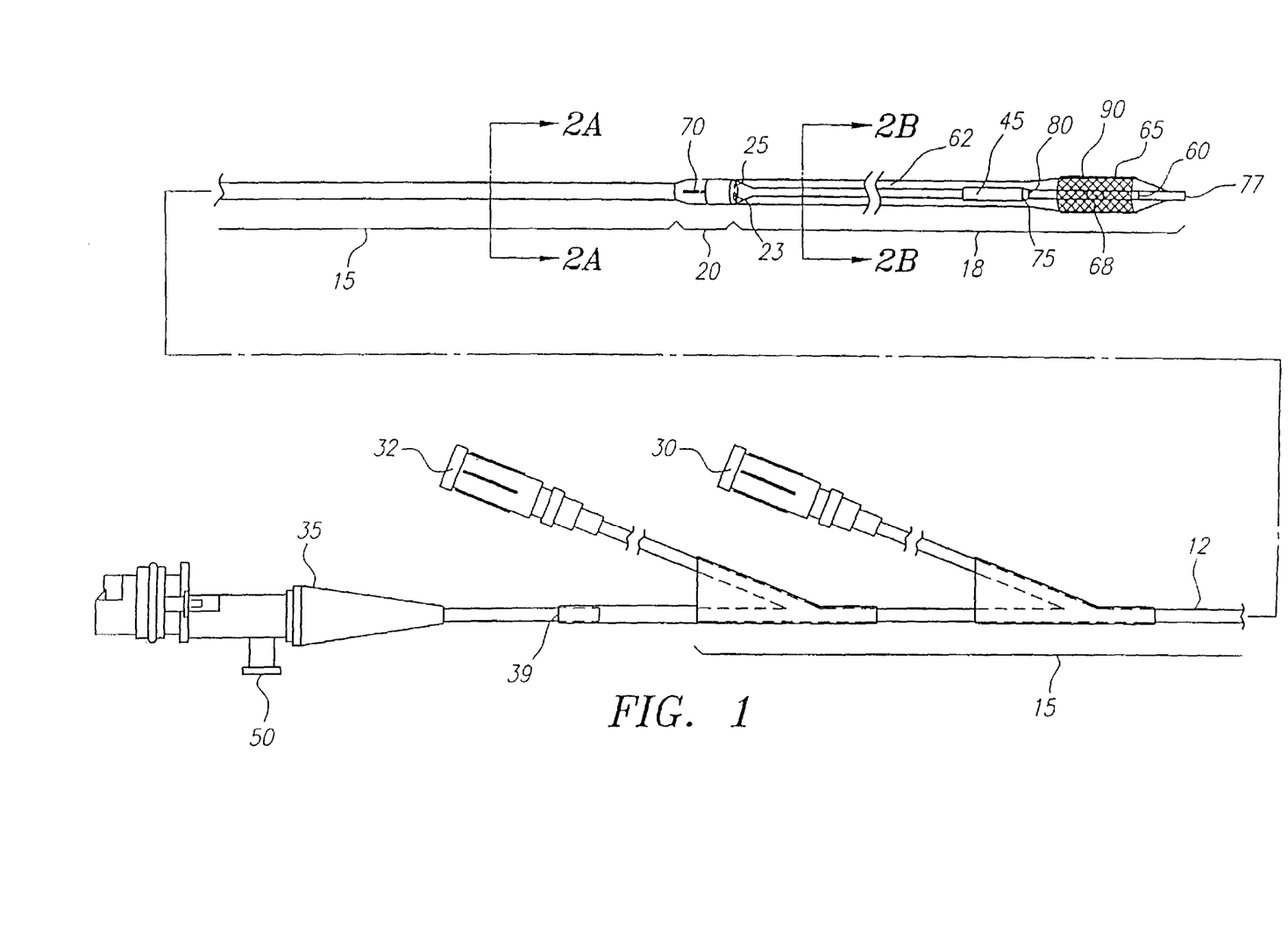
FIG. 1 depicts a preferred embodiment of a catheter according to the present invention.
Figures 2A, 2B, 3:
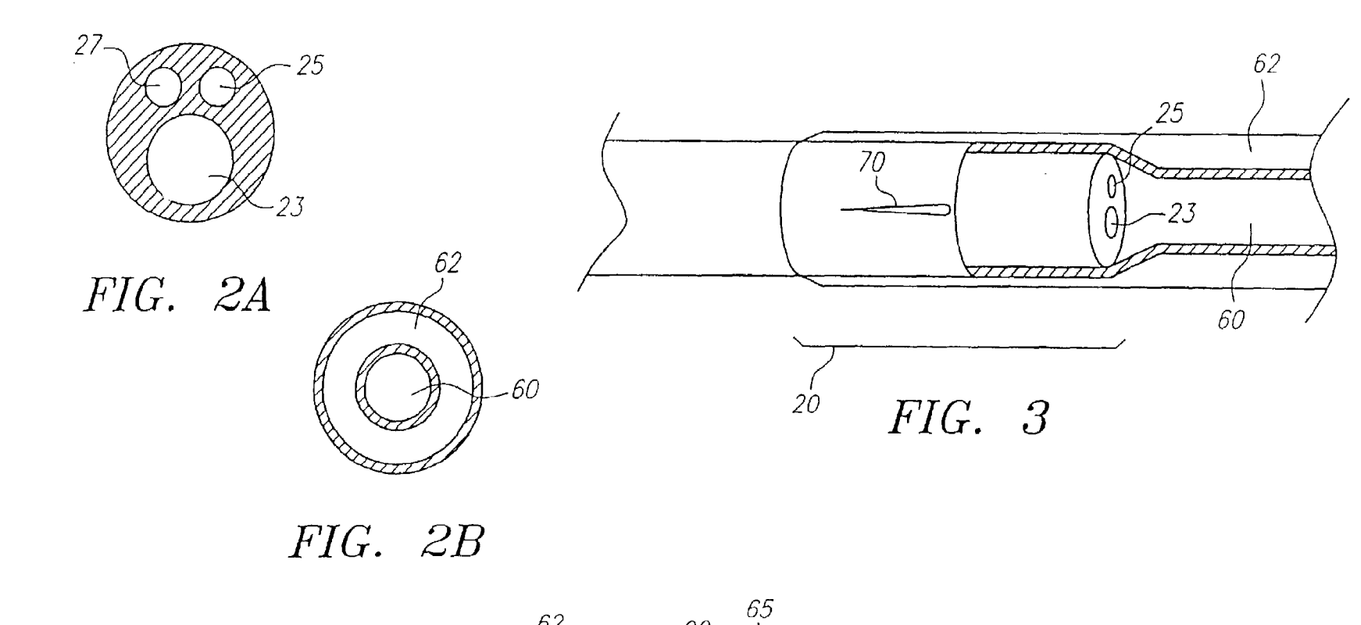
FIG. 2A is a cross-sectional view through section line A—A of the catheter depicted in FIG. 1.
FIG. 2B is a cross-sectional view through section line B—B of the catheter depicted in FIG. 1.
FIG. 3 depicts a transition region between proximal and distal regions of the body of the catheter depicted in FIG. 1.

FIG. 1 depicts a preferred embodiment of a catheter according to the present invention. The catheter has a catheter body 12, which comprises proximal region 15, distal region 18, and transition region 20. FIG. 2A is a cross-sectional view of the proximal region of catheter body 12 through section line A—A. In this embodiment, proximal region 15 has three lumens, work element lumen 23, guidewire lumen 25, and proximal balloon inflation lumen 27. Other embodiments could have still more lumens to accommodate additional imaging or interventional devices, as described generally in co-pending U.S. patent application Ser. No. 07/975,769, filed Nov. 13, 1992, the full disclosure of which is incorporated herein by reference. Guidewire port 30 and balloon inflation port 32 (FIG. 1) place guidewire lumen 25 and proximal balloon inflation lumen 27 in communication with the exterior of the catheter near its proximal end.

In the embodiment depicted in FIG. 1, drive shaft 45 is reciprocatably disposed within work element lumen 23. (For clarity, only a distal portion of drive shaft 45 is illustrated.) At its proximal end, work element lumen 23 is in communication with expandable member 39, which is connected in turn to proximal housing 35. The proximal housing is adapted to connect a proximal end of drive shaft 45 to a drive motor (not shown) for rotating the drive shaft.

Expandable member 39 allows the drive shaft to be conveniently advanced and retracted within work element lumen 23 by moving proximal housing 35 with respect to the catheter body to lengthen or shorten expandable member 39 as desired. Proximal housing 35 is provided further with flush port 50, to allow for the flushing of trapped air bubbles from within work element lumen 23. The construction and use of proximal housing 35 in conjunction with a multi-lumen catheter is more fully described in co-pending U.S. patent application Ser. No. 07/976,228, filed Nov. 13, 1992, the full disclosure of which is incorporated herein by reference.

A cross-section through distal region 18 of catheter body 12 through section line B—B is depicted in FIG. 2B. As can be seen therein, distal region 18 has two concentric lumens. In the distal region, common lumen 60 is disposed within distal balloon inflation lumen 62.

Referring again to FIG. 1, balloon 65 is disposed about common lumen 60. The balloon is in communication with distal balloon inflation lumen 62 to provide for inflation of the balloon. Radiopaque band 68 is wrapped around the common lumen at a position within the balloon to allow for fluoroscopic imaging to assist in placing the balloon within the desired region of the blood vessel. A prosthetic device 90, such as a stent, is disposed about the balloon 65, and is in close radial proximity thereto. Where the prosthetic device is a wire mesh stent composed of metallic material, the distal region of the catheter may be equipped with the stent by crimping the stent onto the distal region of the catheter body, such as over the balloon.

The length of common lumen 60 will generally be between 5 and 30 centimeters, with balloon 65 typically having a length in the range of 1.5–4.5 centimeters. The balloon crossing profile, the minimum width crossable by the balloon when deflated, will typically be in the range of 0.020–0.045 inches. The outside diameter of the balloon when inflated within a blood vessel will commonly be between 1.5 and 4.5 millimeters. The foregoing ranges are set forth solely for the purpose of illustrating typical device dimensions. The actual dimensions of a device constructed according to the principles of the present invention may obviously vary outside of the listed ranges without departing from those basic principles.

FIG. 3 depicts transition region 20 between the three parallel lumens of proximal region 15 and the two concentric lumens of distal region 18. Transition region 20 provides for communication between common lumen 60 of the distal region and both guidewire lumen 25 and work element lumen 23 of the proximal region. Also, distal balloon inflation lumen 62 is placed in communication with proximal balloon inflation lumen 27 through balloon inflation lumen connection 70, which is formed by cutting through the exterior of proximal region 15 to expose a portion of the proximal balloon inflation lumen to close it off from common lumen 60. Thus, a continuous inflation path exists from balloon inflation port 32, through proximal and distal balloon inflation lumens 27 and 62, and into balloon 65. Injection of fluid into balloon inflation port 32 will thereby result in inflation of balloon 65.

It is contemplated that the catheter depicted in FIG. 1 will be used as follows. First, a conventional guidewire will be advanced into the patient's vascular system until it lies within the region of stenosis. Next, the guidewire will be inserted into distal tip 77 (FIG. 1) of the catheter and through common lumen 60 of distal region 18. The catheter will then be advanced into the patient's body over the guidewire until the guidewire reaches transition region 20. At this point, the guidewire will be directed into guidewire lumen 25 and through the proximal region until it exists the catheter through guidewire port 30 as the catheter is advanced further into the patient's body. Eventually, the catheter will be advanced to a point where common lumen 60, balloon 65, and prosthetic device 90 lie within the region of interest.

The operator of the system can then grasp the guidewire at the end protruding from the guidewire port. The operator will pull the guidewire back a short distance into guidewire lumen 25 of proximal region 15 in order to clear common lumen 60 of distal region 18. A work element 75, which will typically be an ultrasonic imaging transducer, fixed to the distal end of drive shaft 45, may then be advanced through work element lumen 23 of the proximal region and into the common lumen of the distal region. Imaging of the region of interest may then take place to ensure that the prosthesis is positioned away from any branching segments of the blood vessel and is anchored on both sides in contact with healthy tissue.

Following imaging, the prosthesis is expanded in the region of interest by inflating the balloon to a desired diameter. Alternatively, where a self-expanding prosthesis is employed, no balloon inflation is needed to expand the prosthesis. After the prosthesis has been expanded, the region of interest may be imaged again to verify that optimal positioning of the prosthesis has occurred and to determine the diameter of expansion achieved by the prosthesis. The prosthesis may then be further expanded if desired, or a second prosthesis having a larger expanded diameter may be installed within the first prosthesis. When proper diameter and positioning of the prosthesis has been achieved, the balloon, if used, is deflated, and the catheter is removed from the region of interest.

FIG. 1 depicts a catheter in which the common lumen is narrowed at a restriction 80 just proximal to the balloon. Distal of the restriction, the common lumen will be just large enough to allow passage of the guidewire. This allows the balloon crossing profile, the width of the catheter in the region of the balloon when not inflated, to be as small as possible. This is advantageous in that it allows the balloon to be advanced into narrow and tortuous regions of the blood vessel. Placing the restriction proximal to the balloon is disadvantageous, however, in that it may prevent entry of the work element into the common lumen within the balloon. Thus, some repositioning of the catheter body within the blood vessel, i.e., advancement of the catheter body further into the blood vessel, may be necessary to allow for imaging of the treated region.

Figure 4:
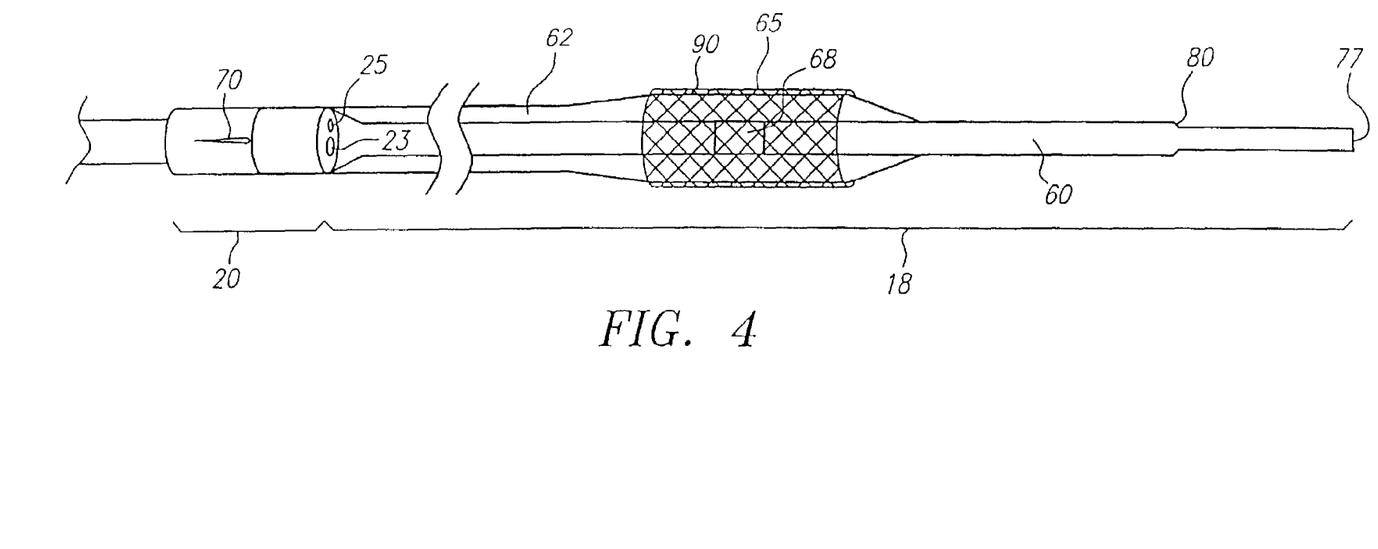
FIG. 4 depicts the transition region and distal region of an alternative preferred embodiment of a catheter according to the present invention.

FIG. 4 depicts the distal region of an alternative preferred embodiment in which the common lumen is not restricted in the region proximal to the balloon and the prosthesis. In this embodiment, the work element may travel through the common lumen into, through, and beyond the balloon. This is advantageous in that it allows for imaging of the blood vessel throughout the region of the prosthesis without repositioning the catheter body.

As discussed above, it is desirable at present to have the guidewire in place within the common lumen during balloon inflation in case rapid withdrawal of the catheter over the guidewire becomes necessary. However, future developments in interventional devices and techniques may make this unnecessary. If this becomes the case, imaging will be possible from within the balloon even while the balloon is being inflated. Of course, an increased diameter common lumen within the balloon requires a slightly larger balloon crossing profile. Some ability to enter narrow regions must thereby be sacrificed in order to achieve a more flexible imaging capability.

The embodiment of FIG. 4 depicts the common lumen having restriction 80 at some distance distal to balloon 65. This restriction will prevent the accidental exit of the work element from the distal tip 77 of the catheter body while still allowing passage of the guidewire. This prevents injury to the blood vessel wall, which might result from accidental contact by the rotating work element. In order to further safeguard against trauma to the blood vessel, distal region 60 and distal tip 77 are preferably constructed of a material which is highly atraumatic; a material which is extremely soft and flexible so that the catheter can be repositioned in the vessel without using a guidewire and without harm to the vessel.

A catheter according to the present invention could also be made to carry an interventional work element such as a rotating cutter or a laser ablation device. In such a case, it would be necessary for the work element to advance beyond the distal tip 77 of the catheter body. In such a catheter system, restriction 80 would be omitted altogether to allow for unhindered passage of the work element.

Figure 5:
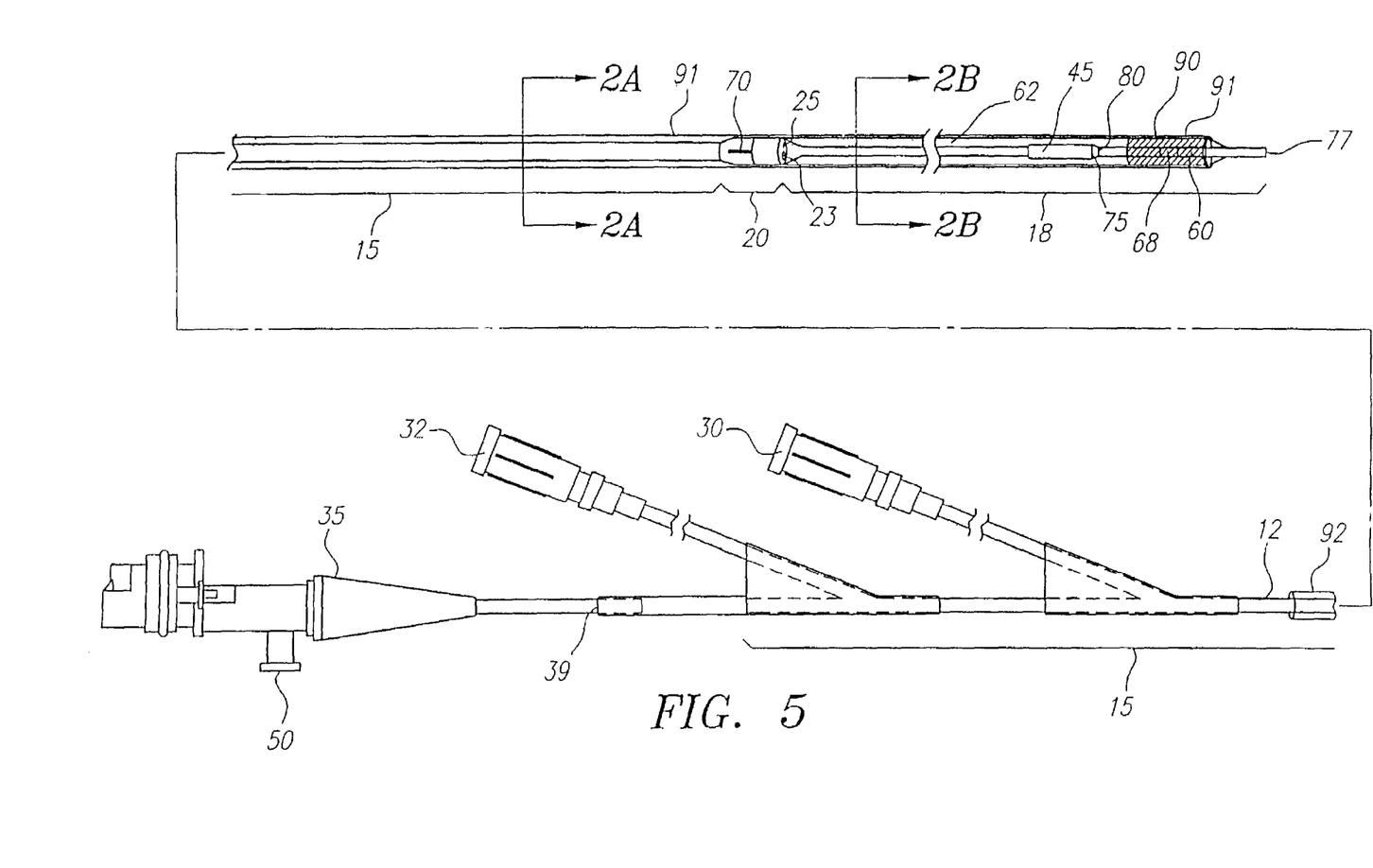
FIG. 5 depicts an alternative preferred embodiment of a catheter according to the present invention.

FIG. 5 depicts the proximal and distal regions of an alternative preferred embodiment which does not require an angioplasty balloon for expansion of the prosthetic device. This embodiment shares certain components with the catheter depicted in FIG. 1, and those common aspects share the same numerals with this earlier-described catheter. The prosthetic device 90 is a self-expanding stent which is disposed on the distal region of the catheter body 12. The stent is held in close radial proximity to the catheter body by a sheath 91 which covers the stent at the distal region of the catheter. In this embodiment, the stent 90 is disposed between the catheter body 12 and the sheath 91. The sheath 91 extends to the proximal region of the catheter body to provide a proximal region 92 of the sheath which allows the sheath to be withdrawn proximally to release the prosthetic device at the region of interest.

Figure 6:
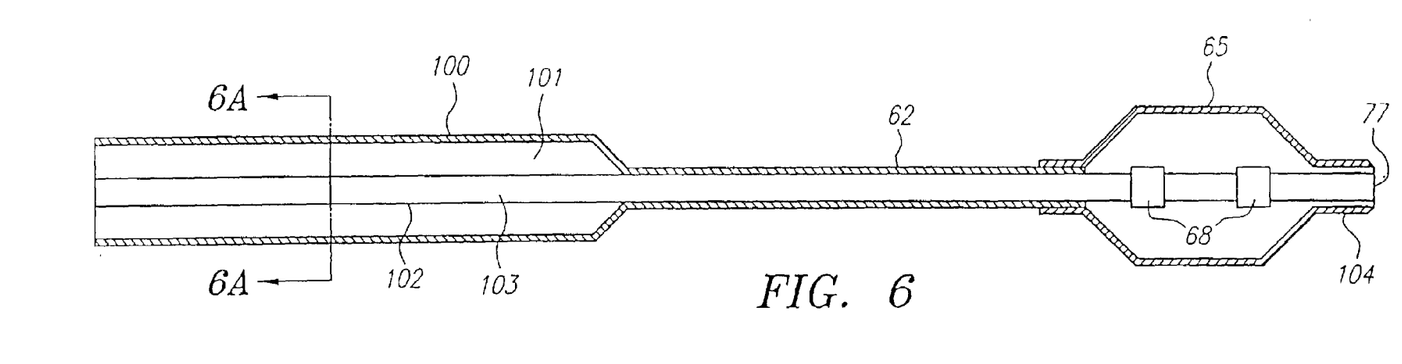
FIG. 6 depicts the transition region and distal region of a single lumen catheter according to the present invention.
Figure 6A:
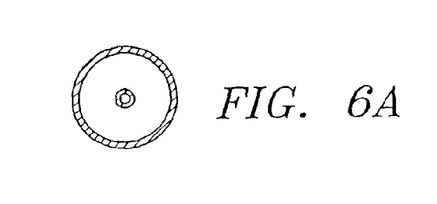
FIG. 6A depicts a cross-sectional view through section line A—A of the catheter depicted in FIG. 6.

FIG. 6 depicts the distal region of another alternative embodiment which does include an angioplasty balloon. This embodiment shares certain components with the catheter depicted in FIG. 4, and those common aspects share the same numerals with this earlier-described catheter. This catheter includes inflation port 101, guidewire lumen wall 102, and guidewire/ultrasound lumen 103 within catheter body 100. The catheter is provided with a short atraumatic region 104 extending beyond the angioplasty balloon 65. FIG. 6A is a cross-sectional view of the proximal region of catheter body 100 through section line A—A. The proximal region has two lumens: one for inflation and one for a guidewire or ultrasound imaging device. A prosthetic device (not shown) is disposed about the angioplasty balloon 65 as shown in FIGS. 1 and 4. In use, the catheter requires that the positioning guidewire be completely withdrawn from the lumen before an imaging device can be inserted therein for the purpose of imaging the prosthesis within a body passageway to determine whether it is positioned longitudinally within an optimal region.

Figure 7:
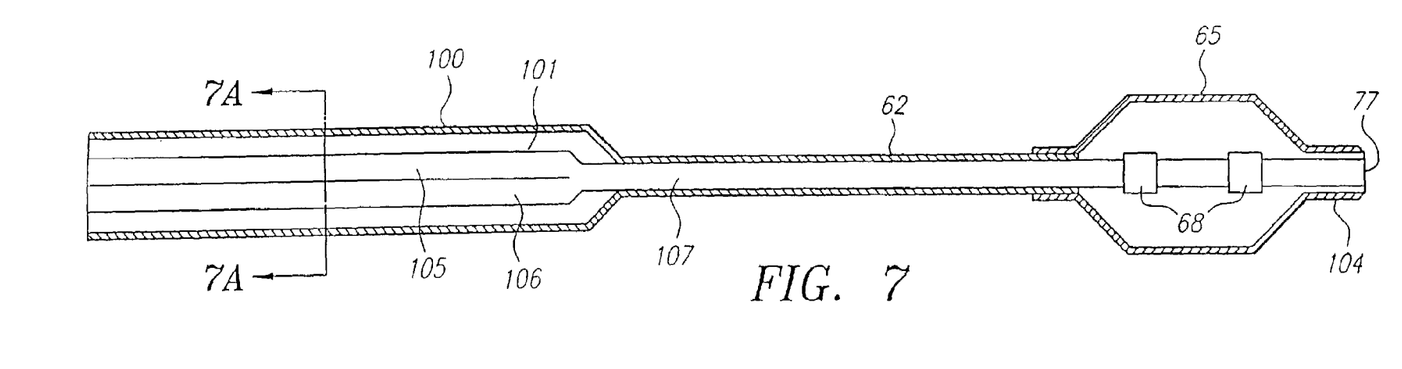
FIG. 7 depicts the transition region and distal region of an alternative common lumen catheter according to the present invention.
Figure 7A:
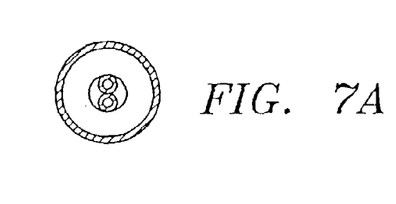
FIG. 7A depicts a cross-sectional view through section line A—A of the catheter depicted in FIG. 7.

FIG. 7 depicts the distal region of another alternative embodiment which also includes an angioplasty balloon. FIG. 7A is a cross-sectional view of the proximal region of the catheter body 100 through section line A—A. The proximal region includes separate lumens 105 and 106 for receiving a guidewire and an ultrasound imaging core. The distal region includes a common lumen 107, the proximal end of which includes a transition region which is in communication with both lumens 105 and 106. The common lumen 107 can alternately receive a guidewire or an imaging core. A prosthetic device (not shown) is disposed about the angioplasty balloon as shown in FIGS. 1 and 4. In use, the catheter is positioned over a guidewire extending through the guidewire lumen and the common lumen. The guidewire is then withdrawn proximal beyond the transition region, and is housed in the guidewire lumen, leaving the common lumen open to receive an imaging core. The imaging core is then advanced into the common lumen and used to position the prosthesis within the body passageway.

Figure 8:
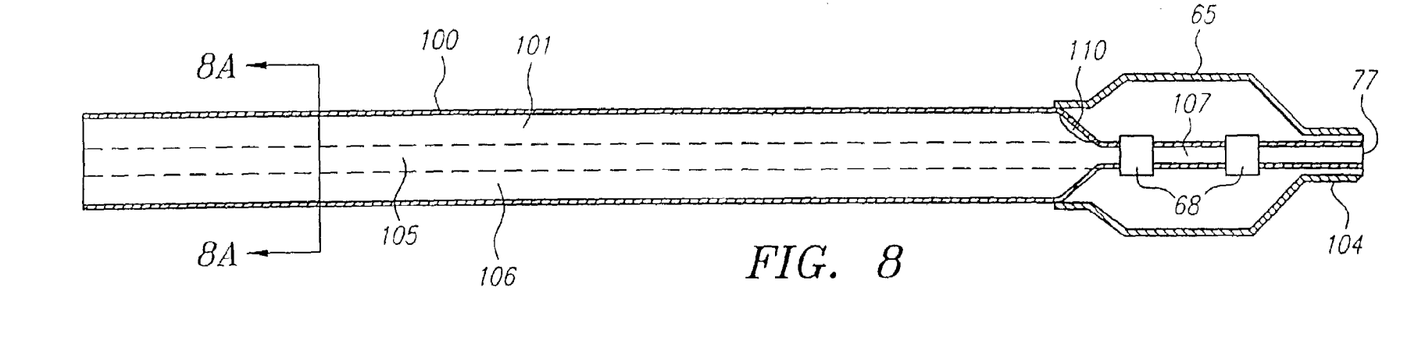
FIG. 8 depicts the transition region and distal region of an alternative common lumen catheter according to the present invention.
Figure 8A:
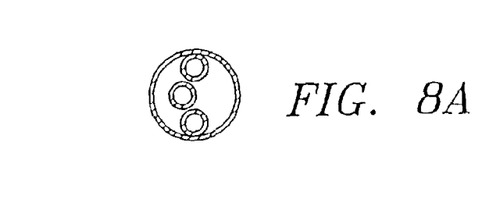
FIG. 8A depicts a cross-sectional view through section line A—A of the catheter depicted in FIG. 8.

FIG. 8 depicts the distal region of another alternative embodiment which shares many components with FIG. 7, and these common aspects share the same numerals. FIG. 8A is a cross-sectional view of the proximal region of the catheter body 100 through section line A—A. Inflation lumen 101 is in communication with balloon 65 through pore 110. Wire lumen 105 and ultrasound lumen 106 merge into common lumen 107 at the distal region of the catheter. The catheter of FIG. 8 has a short common lumen 107. This catheter allows for exchange of the imaging core for the guidewire with only minimal withdrawal of the guidewire. A prosthetic device (not shown) is disposed about the angioplasty balloon as shown in FIGS. 1 and 4.

Figure 9:
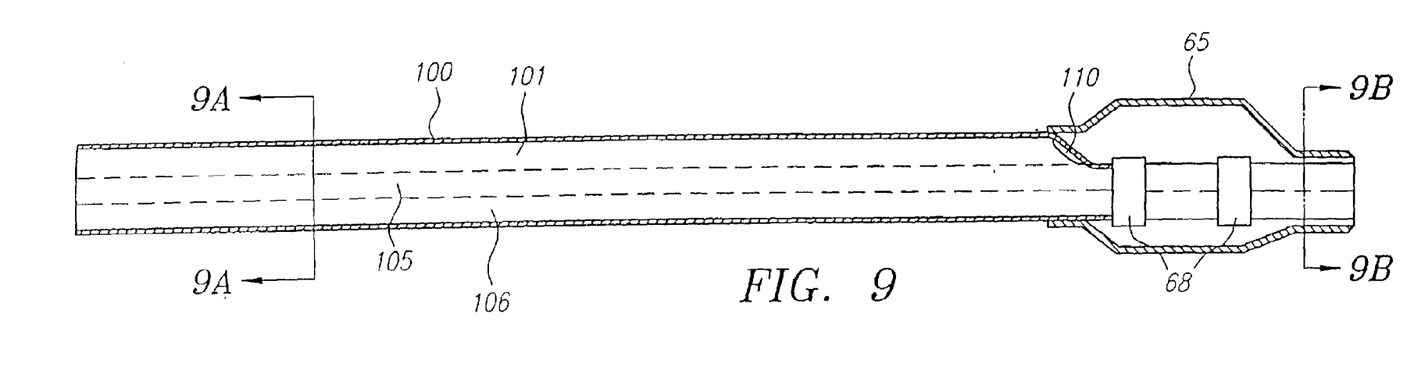
FIG. 9 depicts the distal region of a dual lumen catheter which does not have a common lumen according to the present invention.
Figure 9A:
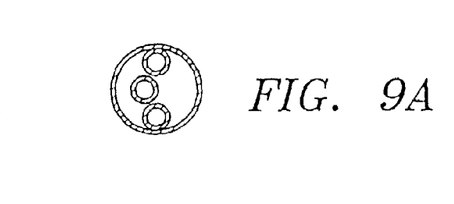
FIG. 9A depicts a cross-sectional view through section line A—A of the catheter depicted in FIG. 9.
Figure 9B:
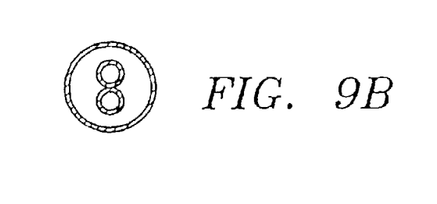
FIG. 9B depicts a cross-sectional view through section line B—B of the catheter depicted in FIG. 9.

FIG. 9 depicts the distal region of another alternative embodiment which shares many components with FIG. 8, and these common aspects share the same numerals. FIG. 9A is a cross-sectional view of the proximal region of the catheter body 100 through section line A—A, while FIG. 9B is a cross-sectional view of the distal region of the catheter beyond the balloon 65 through section line B—B. In this embodiment, the guidewire lumen 105 and the ultrasound lumen 106 extend as separate lumens through the entire distal end of the catheter. There is no transition region and no common lumen. The guidewire lumen may extend proximally to the proximal end of the catheter. Alternatively, the guidewire lumen may terminate in the distal region of the catheter or just proximal thereto so as to include a monorail design as disclosed by Yock, U.S. Pat. No. 5,350,395, which is expressly incorporated herein by reference. In use, this catheter allows positioning over a guidewire, followed by imaging of a prosthesis (not shown) without repositioning or withdrawing the guidewire. Accordingly, the guidewire can be left in place in the guidewire lumen while imaging takes place in the ultrasound lumen. Image artifacts may be observed when such use is undertaken, but can be eliminated by withdrawing the guidewire a small distance during imaging.

The ultrasonic transducer device for use with catheters herein include removable imaging cores as disclosed in Crowley et al., U.S. Pat. No. 4,951,677, Griffith et al., U.S.

Pat. No. 5,115,814, and Sieben, U.S. Pat. No. 5,353,798, all of which are expressly incorporated herein by reference. The imaging devices also may include non-removable imaging cores as disclosed by Sieben et al., U.S. Pat. No. 5,243,988, incorporated herein by reference, which include an intravascular imaging device having an ultrasonic sensor located at a distal end of an intravascular wire sized and adapted to be located within the guidewire lumen of conventional catheters used for intravascular procedures. As such, the imaging cores have several significant advantages. For example, the imaging core can utilize the path provided by the guidewire lumen of a conventional catheter to image at the arterial location to which the catheter is advanced. Moreover, in several embodiments, the imaging core may be provided with conventional guidewire features, e.g., a floppy spring tip, to enable the imaging guidewire to be used as both a conventional guidewire for positioning an intravascular catheter as well as imaging features, e.g., a sensor, to enable imaging the intravascular regions accessible thereby.

Figure 10:
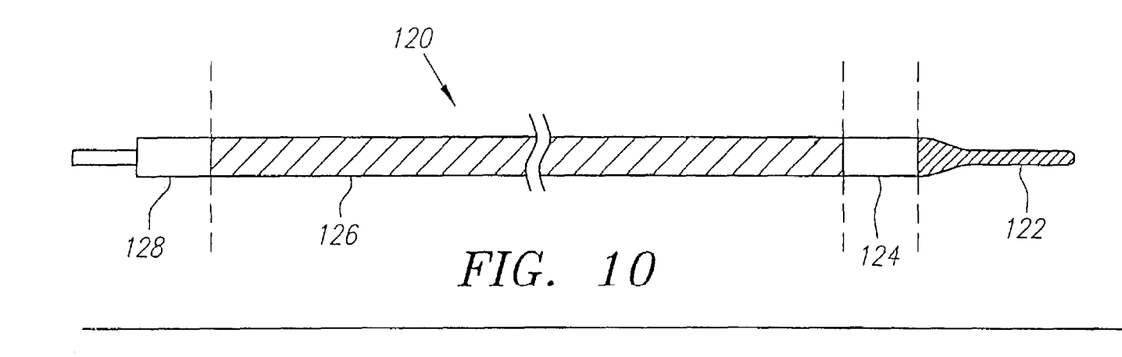
FIG. 10 depicts a removable imaging core according to the present invention.

In order to be utilized in the above-described manner, an embodiment of the imaging core 120 is provided, as shown in FIG. 10. The imaging core 120 includes a tip section 122, a sensor section 124, a drive cable section 126, and a proximal connector section 128. As mentioned above, an essential requirement for the imaging core is that it possess an outer profile of a size that allows it to fit through a guidewire lumen in conventional interventional catheters. In catheters that use 0.018 inch guidewires, the guidewire lumen has a diameter typically in a range between 0.020 and 0.022 inches. The diameter of the proximal section 128 of the imaging core 120 may be as large as 0.020 inches, but the rest of the imaging core should be not more than approximately 0.018 inches. For use with catheters designed with guidewire lumens of other sizes, relative adjustments in dimension apply.

Figure 11:
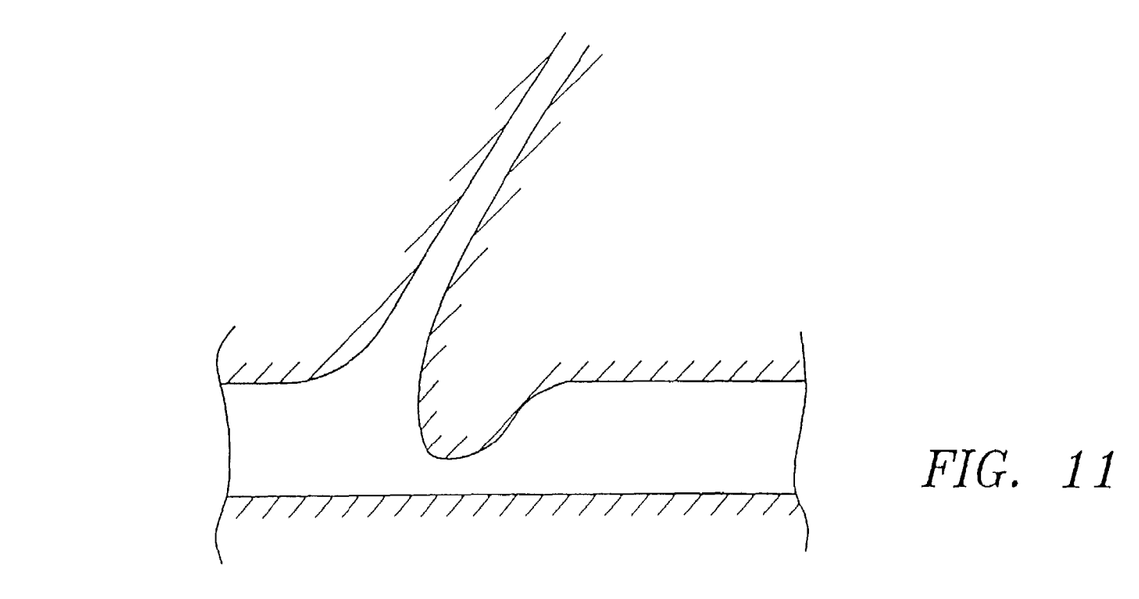
FIG. 11 depicts a vessel having blockage near a branching segment.
Figure 12:
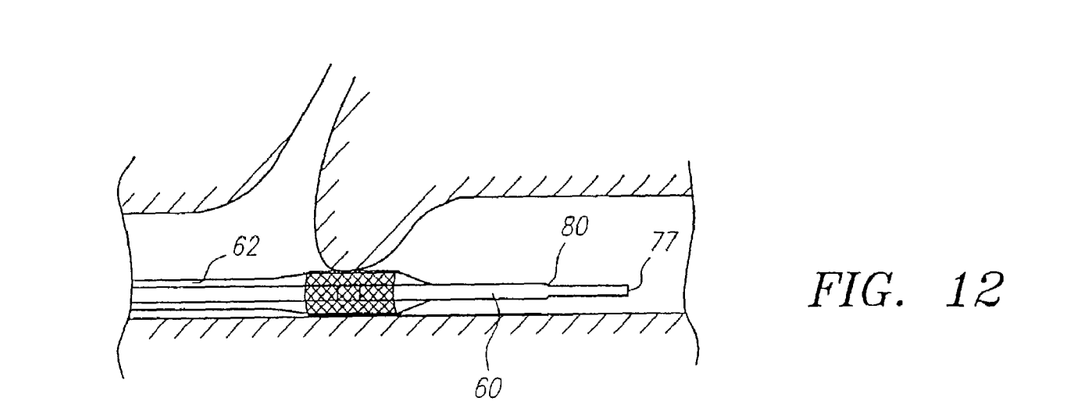
FIGS. 12, 13, and 14 depict a method of treating a diseased region of a vessel in accordance with methods and structures disclosed herein.
Figure 13:
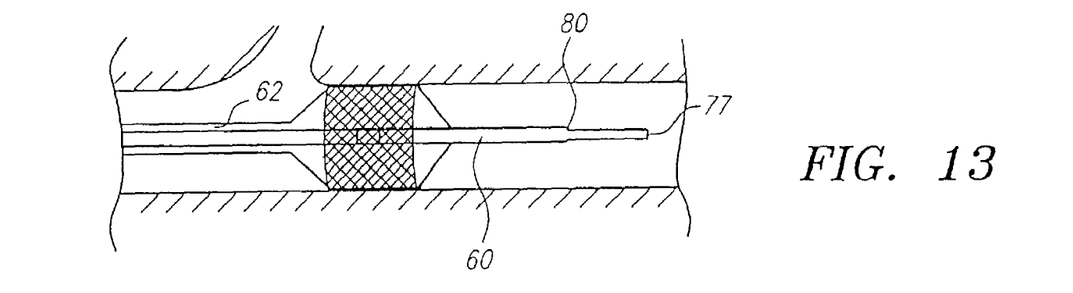
Figure 14:
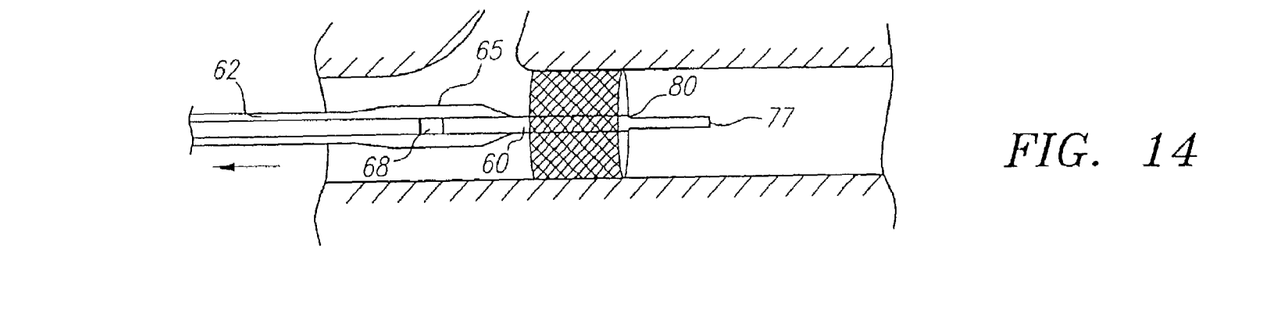

The catheters and methods disclosed herein are particularly well adapted for treatment of vascular stenosis positioned in close proximity to a branching segment of a blood vessel as depicted in FIG. 11. In use, the catheter is positioned over a guidewire as shown in FIG. 12 in the region of a body passageway having a stenosis. With the aid of ultrasound imaging through lumen 60 which extends through the prosthetic device, the prosthesis is positioned to cover the stenosis but to avoid the branching segment of the vessel. The prosthetic device is then expanded in the region of interest as shown in FIG. 13. The stent is left in place while the catheter is removed from the region of interest. The stent holds the lumen at an expanded diameter.

Although the foregoing invention has, for purposes of clarity of understanding, been described in some detail by way of illustration and example, it will be obvious that certain changes and modifications may be practiced which will still fall within the scope of the appended claims.

What is claimed is:

1. A method for treating a patient comprising:
    inserting a self-expandable prosthesis into a body passageway of the patient;
    positioning the self-expandable prosthesis within the body passageway to lie at or near an area of interest;
    expanding the self-expandable prosthesis to a first diameter at the area of interest;
    without removing the self-expandable prosthesis from the area of interest, imaging at least a portion of the body passageway by using an imaging device within the body passageway after the step of expanding the self-expandable prosthesis;
    inserting a second prosthesis into the self-expandable prosthesis in the area of interest if the first diameter is not sufficiently large; and
    using the second prosthesis to expand the self-expandable prosthesis to a second diameter larger than the first diameter.

2. The method of claim 1, wherein the self-expandable prosthesis includes a self-expandable stent.

3. The method of claim 2, wherein the self-expandable stent comprises a wire mesh tube having a collapsed diameter which permits the stent to be disposed upon a catheter, and inserted into the body passageway, wherein the wire mesh tube can be expanded to the first expanded diameter.

4. The method of claim 1, wherein the second prosthesis includes a catheter having an inflatable balloon disposed about the distal region of the catheter.

5. The method of claim 4, wherein the step of expanding the second prosthesis includes inflating the balloon to controllably expand the self-expandable prosthesis at the area of interest.

6. The method of claim 1, further comprising the step of imaging at least the self-expandable prosthesis after the first expanding step.

7. The method of claim 1, further comprising the step of imaging at least a portion of the body passageway before the first expanding step.

8. The method of claim 1, wherein the first expanding step includes imaging at least the self-expandable prosthesis.

9. The method of claim 1, further comprising the step of imaging at least a portion of the body passageway prior to the step of expanding the second prosthesis.

10. The method of claim 1, further comprising the step of imaging at least the self-expandable prosthesis prior to the step of expanding the second prosthesis.

11. The method of claim 1, wherein the step of expanding the self-expandable prosthesis to a first diameter includes withdrawing a sheath to expand the self-expandable prosthesis.

* * * * *